US008354098B2

(12) United States Patent
Philbin et al.

(10) Patent No.: US 8,354,098 B2
(45) Date of Patent: Jan. 15, 2013

(54) CLEAR HAIR GEL FIXATIVES

(75) Inventors: Michael T Philbin, Hopewell, NJ (US); Stephanie M. Murphy, Thomhurst, PA (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 13/128,423

(22) PCT Filed: Nov. 17, 2009

(86) PCT No.: PCT/EP2009/065325
§ 371 (c)(1),
(2), (4) Date: May 10, 2011

(87) PCT Pub. No.: WO2010/057887
PCT Pub. Date: May 27, 2010

(65) Prior Publication Data
US 2011/0217256 A1 Sep. 8, 2011

Related U.S. Application Data

(60) Provisional application No. 61/115,668, filed on Nov. 18, 2008.

(30) Foreign Application Priority Data

Mar. 4, 2009 (EP) .................... 09154321

(51) Int. Cl.
*A61K 8/81* (2006.01)
*A61K 8/02* (2006.01)
*A61Q 5/06* (2006.01)
(52) U.S. Cl. .................... 424/70.17; 424/401
(58) Field of Classification Search ............ 424/70.17, 424/401
See application file for complete search history.

(56) References Cited

U.S. PATENT DOCUMENTS

| | | | |
|---|---|---|---|
| 3,519,701 A * | 7/1970 | Wagner et al. | 525/61 |
| 4,421,602 A | 12/1983 | Brunnmueller et al. | |
| 4,880,618 A * | 11/1989 | Grollier et al. | 424/43 |
| 5,977,274 A | 11/1999 | Leblanc et al. | |
| 6,541,573 B1 | 4/2003 | Niessner et al. | |
| 2002/0048603 A1 | 4/2002 | Burmeister et al. | |
| 2003/0199642 A1 | 10/2003 | Schneider et al. | |
| 2004/0151683 A1* | 8/2004 | Kalbfleisch et al. | 424/70.13 |
| 2006/0153793 A1 | 7/2006 | Chrisstoffels | |

FOREIGN PATENT DOCUMENTS

| | | |
|---|---|---|
| EP | 0 879 590 A2 | 11/1998 |
| EP | 1 313 432 B1 | 5/2003 |
| EP | 1 646 663 B1 | 4/2006 |
| JP | 2003-095893 * | 3/2003 |
| WO | WO 2005 002532 * | 1/2005 |
| WO | WO 2005/002532 * | 1/2005 |
| WO | WO 2005/002532 A2 | 1/2005 |

OTHER PUBLICATIONS

"Celvol® Polyvinyl Alcohol" product information from Celanese, 2007, pp. 1-16.*
International Search Report for PCT Application No. PCT/EP2009/065325; Completion date Feb. 16, 2010.
European Search Report for Application No. 09154321.5; Completion date Aug. 7, 2009.

* cited by examiner

*Primary Examiner* — Aradhana Sasan
(74) *Attorney, Agent, or Firm* — Norris McLaughlin & Marcus, P.A.

(57) ABSTRACT

This invention details the use of a simple blend of polyvinyl formamide and one or more polyvinyl alcohols as the fixative polymer system in a clear hair gel composition. The interaction of the polymer system and gelling agents provides clarity of less than 20 NTU and other physical properties such as good curl compression, resistance to high humidity and resistance to flaking.

19 Claims, No Drawings

CLEAR HAIR GEL FIXATIVES

This application is a National Phase Application of PCT Application No. PCT/EP2009/065325, filed Nov. 17, 2009, and claims priority to U.S. Provisional Patent Application Ser. No. 61/115,668 filed on Nov. 18, 2008 and EP Application No. 09154321.5, filed Mar. 4, 2009, all of which are incorporated herein by reference in their entireties.

FIELD OF INVENTION

Clear hair gel fixatives have been desired for many years, as consumers perceive that clear represents purity and quality in hair care products. Yet the challenge has always been towards getting more than just clarity. Other properties such as curl strength or hold (also referred to as stiffness) and resistance to humidity are just as important to hair styling products. The current invention deals with a blend of safe and readily available polymers to afford the formulator clear compositions with superior hold and humidity resistance.

BACKGROUND OF THE INVENTION

For many years clarity in personal care products has been synonymous with purity as pure water is represented by crystal clear. Yet in striving for clarity other properties have taken a back seat in the quest for clarity. The hardest of all applications to obtain this clarity has been in the gelled hair products. Gels are typically formed by association or cross-linking of polymers to structure the liquid portion of the formulation. These associates can potentially act like crystal regions and their formation tends to make the gels opaque as the formation of crystals scatters light. Additionally, any incompatibility of the styling polymers with the gelling agent may also adversely affect the clarity.

One approach to increase the clarity in gelled products is to reduce the molecular weight of the polymeric material, as it is well know that lower molecular weight provides better clarity in both solution and gel. The drawback to low molecular weight is that the polymers are less able to provide good physical properties once the liquid has dried. Properties such as curl strength (stiffness) and humidity resistance will suffer as the molecular weight of the polymer system is lowered.

To overcome the deficiencies of low molecular weight some specialty tertiary polymers were prepared. And while these worked well to provide all the properties the cost of such specialized polymers have been prohibitive to the hair care marketplace. There still exist in the market place today a need for a system for providing hold and humidity resistance from clear gelled fixative systems that are safe and made from in-expensive, readily available ingredients.

BRIEF DESCRIPTION OF THE INVENTION

It has now been found that very specific blends of polyvinyl alcohol (PVOH) and polyvinyl formamide (PVF) in specific ratios, molecular weights and degree of hydrolysis can provide all the desired properties in hair gel systems while maintaining clarity. The properties of interest to most users of hair fixatives (also known as styling compounds) is that the hair be able to hold or set in place which is measured in the lab using curl compression, and the ability of the styling gel to resist humidity while on the hair (resist droop). This humidity resistance is particularly difficult to obtain since all the hair styling compounds must be able to be removed in the shower by the action of shampoo and water.

Beyond the physical properties, the styling gel must leave the hair looking natural and resist flaking and peeling while being worn. Flaking would provide the appearance of dandruff on ones clothing and would be highly undesirable. Peeling would provide the hair with an unnatural and dull look.

The blends of PVOH and PVF of the current invention have been shown to provide excellent hold, as measured by curl compression and humidity resistance. Surprisingly these blends are very resistant to flaking and peeling and provide the hair a natural look.

DETAILED DESCRIPTION OF THE INVENTION

The instant invention comprises a blend of one or more grades of polyvinyl alcohol, polyvinyl formamide and water. The PVOH provides humidity resistance while the PVF provides a high level of clarity, resistance to flake and good curl compression. Polyvinyl Alcohol is commercially available from a number of different sources, one being Celanese Chemicals (1601 West LBJ Freeway, Dallas Tex.) which offers a wide variety of grades. Grades of PVOH differ by molecular weight and degree of hydrolysis. Molecular weight is expressed in terms of viscosity and comes in low (3-5 mPas), medium (15-35 mPas), and high (above 50 mPas). In one embodiment of this invention the molecular weight is either low or medium. In another embodiment the molecular weight is low.

Polyvinyl alcohol is derived from polyvinyl acetate by alkaline hydrolysis of the ester groups, thus the term degree of hydrolysis. Therefore a PVOH with a degree of hydrolysis of 88% means there are still 12% acetate groups on the polymer. The degree of hydrolysis also changes the properties of the PVOH. For purposes of the application PVOH is available in five different grades, low hydrolysis (78-85%), partially hydrolyzed (87-89%), intermediate hydrolyzed (90-97%), fully hydrolyzed (98-99%) and super hydrolyzed (greater than 99%). In one embodiment of the invention the PVOH will be between partially hydrolyzed to fully hydrolyzed (87 to 99%). In another embodiment the PVOH will be partially hydrolyzed.

Polyvinyl formamide (PVF) can be made by a variety of methods and in different solvents. The process of making PVF is described in detail in U.S. Pat. No. 5,977,274 to Leblanc et al. and is incorporated herein by reference. Other publications that describe various aspects of the synthesis of PVF are U.S. Pat. No. 6,541,573 and U.S. Pat. No. 4,421,602 both. For the PVF to afford good performance the molecular weight is desired to be as high as possible. In one embodiment of this invention the molecular weight of the PVOH will be between 100,000 and 300,000 daltons as measured by Gel Permeation Chromatography.

For purposes of this application, clarity is any level of turbidity less than 20 at 3% polymer solids dissolved in water with 0.6% Carbopol as the thickener which has been neutralized with AMP (see experimental section below for details). The test is conducted by passing a beam of light through a hair gel formulation and measuring the percentage of light loss. When the NTU (nephelometric turbidity units, a measure of turbidity) is less than 20 the hair gel is said to be clear. In one embodiment of this invention, the turbidity of a clear hair gel is less than 15 NTU.

Curl compression is a test to see the amount of stiffness in a swatch of hair 15 centimeters long. The hair is treated with the styling gel and then rolled into a tight curl. The force required to compress the curl 30% of its original diameter is measured. The value is normalized to a standard K90 sample and reported as a percent of standard. This standardization is to take into account variations in handling, hair quality and other variables. It is desirable for the curl compression to be as high as possible, but at least similar to the standard. In one embodiment of this invention, the curl compression is 0.8 (80%) or greater than the K90 sample. In a second embodiment the curl compression is 0.9 (90%) or greater that the K90 standard.

The high humidity curl retention relates to the humidity resistance of a swatch of hair 25 centimeters long. The hair is treated with the styling gel, rolled and then suspended from one end. The hair is subjected to a constant relative humidity of 90% (at a temperature of 21° C.) for 24 hours and the length is measured and reported as a percent of the original swatch. Ideally the curl retention would be as close to the initial as possible to provide the wearer a sag resistant hair style regardless of the weather conditions. In one embodiment of this invention the high humidity curl retention is greater than 50%. In a second embodiment the high humidity curl retention is greater than 70%. In a third embodiment the high humidity curl retention is greater than 90%.

Another very important property of styling gels is their ability to resist flaking from the hair during wearing or combing. Such flaking would cause wearer to experience white powdery looking material that would result in a styling gel that has a high flake. These flakes would give the perception of someone with dandruff and is a property that is highly desirable to avoid. The flake test is a measurement of how much styling gel is fluffed off a sample of hair with a controlled combing and then expressed as a percentage of the control (K90). In one embodiment the flake will be less than the standard (100%). In a second embodiment of this invention the flake will be less than 80% of the standard.

In virtually all clear hair gels there exists various ingredients, as illustrated in the formulation below. In this invention the polymeric fixative is defined as a mixture of polyvinyl formamide and one or more grades of polyvinyl alcohol. The ratio of PVOH to PVF in the polymer fixative will range from 20 to 80% PVOH and 20 to 80% PVF. In one embodiment of this invention the ratio of PVOH to PVF in the polymer fixative will range from 40 to 70% PVOH and 30 to 60% PVF.

For some applications blends of more than one grade of PVOH can be used. Therefore blends of low molecular weight PVOH with medium molecular weight or fully hydrolyzed. PVOH with partially hydrolyzed PVOH offers the formulator options to obtain variations in properties as needed for individual hair styling gells. In an embodiment the invention is a blend of low molecular weight, partially hydrolyzed PVOH with a medium molecular weight with a partially hydrolyzed PVOH is used at a ratio of from 1 to 1 to 4 to 1.

The hair fixative formulations of this invention comprise an amount of the hair fixative polymer which is effective to impart hair fixative properties to the gels. Where the level of polymer is too high, the gels and films formed therefrom exhibit unacceptable haziness. Where the level of polymer is too low, properties such as stiffness and humidity resistance are adversely affected. In one embodiment, the gels comprise from about 0.5 to about 15 weight percent of the polymer (based on the total weight of the gel). In another embodiment the fixative polymer is present from about 1 to 10 weight percent. In a third embodiment the fixative polymer is present at 2 to 7 weight percent of the gel.

Additionally there will be a gelling agent present to provide the proper textural aspects. The gels comprise from 0.05 to about 1 weight percent of the gelling agent. In one embodiment, the gelling agent is present at 0.1 to 0.6 weight percent based on the total weight of the hair fixative gel.

Examples of such gelling agents include synthetic polymers such as the acrylic-based Carbopol® series of thickeners available from B.F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In an embodiment of this application the gelling agent will be Carbomer. In a second embodiment the gelling agent is Carbopol 940 or 908. Carbomer (otherwise known as Carbopol) is a polymer of acrylic acid which has some level of cross-linking. Depending on the grade, the level of cross-linking will vary. Additional monomer(s) can also be added during the polymerization to provide other properties and various grades.

In order for the Carbomer to function as a gelling agent the acid groups must be neutralized with a base such as hydroxide or amine. In one embodiment of the current invention the neutralizing agents are chosen from the list of triethanolamine (TEA), 2-animo-2-methyl-1-propanol (AMP), ammonia and sodium hydroxide. In a second embodiment, the neutralizing agent is TEA or AMP. In a third embodiment the neutralizing agent is AMP.

Other materials can be added to the clear hair gel formulation that will affect the look of the gel, but will not have any significant impact on the properties defined above. The ingredients are, but not limited to, colorants, fragrances, fillers, pigments, conditioners and other actives. One skilled in the art will realize that compatibility of these other ingredients with the styling polymers and gelling agent will ultimately affect the clarity of the final formulation, therefore care must be taken to insure a clear product by careful choice of ingredients.

The following examples are presented to further illustrate the invention. They are not meant to limit or in any way define the scope and utility of this invention.

EXPERIMENTAL

Raw Materials

Polyvinyl alcohol from Celanese
Celvol 523: 87-89% hydrolyzed, viscosity at 4% solids, 20° C. is 23.0-27.0 cPs
Celvol 325: 98-99% hydrolyzed, viscosity at 4% solids, 20° C. is 28.0-32.0 cPs
Celvol 203: 87-89% hydrolyzed, viscosity at 4% solids, 20° C. is 3.5-4.5 cPs
Carbomer from Lubrizol (formerly Noveon)
Carbopol 980: crosslinked polyacrylate
DMDM Hydantoin from Lonza
Glydant Plus Liquid: 100% solids
2-Amino-2-methyl-1-propanol from Angus Chemical Company
AMP-95: 95% solids in water
Triethanolamine from Huntsman Corporation, East Lansing, Mich. 48823-5691
  Gel Formulation (general):
3% total polymer
0.6% Carbomer
0.5% AMP-95
0.5% Glydant Plus Liquid

Example 1

High Viscosity Polyvinyl Alcohol Cook (Celvol 325 or Celvol 523, Celanese)

A one liter 3-neck round bottom flask was equipped with a condenser, temperature probe, heating mantle, and overhead stirrer. Deionized water (450.0 grams) was added to the flask and the stir rate was set at 350 rpm. Polyvinyl alcohol (50.0 grams) was added slowly to the flask to make a 10% solids solution. The polyvinyl alcohol was cooked out at 90° C. for 30 minutes. The final solution was cooled to 40° C. before being discharged from the flask.

Example 2

Low Viscosity Polyvinyl Alcohol Cook (Celvol 203)

The same procedure as in Example 1 except 150.0 grams of polyvinyl alcohol was added to 350 g of water to make a 30% solids solution.

Example 3

Gel Formulation (Tertiary Blend)

Part A—Polymer Solution

A 250 milliliter beaker was equipped with a paddle bladed overhead stirrer.

Deionized water (32.2 grams) was added to the beaker and the stir rate was set at 350 rpm. Polyvinyl formamide (0.5 grams, 100% solids) was added to the beaker and allowed to stir until fully dissolved. Low viscosity polyvinyl alcohol (Celvol 203, 4.2 grams, 30% solids), medium viscosity polyvinyl alcohol (Celvol 523, 12.6 grams, 10% solids), DMDM Hydantoin (Glydant Plus Liquid, 0.5 grams) and 2-amino-2-methyl-1-propanol (AMP-95, 0.5 grams) were added to the beaker.

Part B—Carbomer Solution

Carbomer (Carbopol 980, 30.0 grams of 2% solution) and deionized water (20.0 grams) were added to a 100 milliliter beaker equipped with a magnetic stirrer. A stir plate was used to mix the solution at 400 rpm until homogeneous.

Add Part B to Part A to form a gel. Allow the gel to stir at 350 rpm for 10 minutes.

Example 4

Additional Gel Formulations

Using the procedure from example 3, the following substitutions were made in Part A:

TABLE 1

Hair gel formulation

| Sample # | Polyvinyl formamide (grams) | Celvol 523 (grams of 10% soln) | Celvol 325 (grams of 10% soln) | Celvol 203 (grams of 30% soln) | AMP (gram) | DI Water (grams) |
|---|---|---|---|---|---|---|
| 1 | 3.0 | 0 | 0 | 0 | 0.5 | 46.5 |
| 2 | 0 | 30 | 0 | 0 | 0.5 | 19.5 |
| 3 | 0 | 0 | 30 | 0 | 0.5 | 19.5 |
| 4 | 0 | 0 | 0 | 10 | 0.5 | 39.5 |
| 5 | 2.0 | 10.0 | 0.0 | 0.0 | 0.5 | 37.5 |
| 6 | 1.0 | 20.0 | 0.0 | 0.0 | 0.5 | 28.5 |
| 7 | 2.0 | 0.0 | 10.0 | 0.0 | 0.5 | 37.5 |
| 8 | 1.0 | 0.0 | 20.0 | 0.0 | 0.5 | 28.5 |
| 9 | 2.0 | 0.0 | 0.0 | 3.3 | 0.5 | 44.2 |
| 10 | 1.0 | 0.0 | 0.0 | 6.7 | 0.5 | 41.8 |
| 11 | 1.3 | 12.6 | 4.8 | 0.0 | 0.5 | 30.8 |
| 12 | 0.5 | 12.6 | 12.6 | 0.0 | 0.5 | 23.8 |
| 13 | 1.3 | 4.8 | 12.6 | 0.0 | 0.5 | 30.8 |
| 14 | 1.3 | 12.6 | 0.0 | 1.6 | 0.5 | 34.0 |
| 15 | 0.5 | 12.6 | 0.0 | 4.2 | 0.5 | 32.2 |
| 16 | 1.3 | 4.8 | 0.0 | 4.2 | 0.5 | 39.2 |

Example 5

Measurement of Turbidity

Turbidity

Tubidity of the hair gels was determined using a Hach (Loveland, Colo.) Model 2100N turbidimeter by placing a 30 mL vial containing the hair gel in the sample compartment of the turbidimeter. Note that the hair gel sample needs to be free of any air bubbles to get an accurate reading.

TABLE 2

Turbidity Measurements

| Sample; | Turbidity (NTU) | Expected Turbidity | Synergy |
|---|---|---|---|
| 1 | 5 | | |
| 2 | 50 | | |
| 3 | 64 | | |
| 4 | 11 | | |
| 5 | 7 | 20 | 13 |
| 6 | 25 | 35 | 10 |
| 7 | 12 | 25 | 13 |
| 8 | 34 | 44 | 10 |
| 9 | 3 | 7 | 4 |
| 10 | 4 | 9 | 5 |
| 11 | 18 | 34 | 16 |
| 12 | 36 | 48 | 12 |
| 13 | 19 | 37 | 18 |
| 14 | 23 | 25 | 2 |
| 15 | 36 | 26 | −10 |
| 16 | 12 | 15 | 3 |

The results reported in table 2 above show the actual value obtained in column 2 and the expected value in column 3. The expected is a weighted average from the samples in 1 through 4. The synergy, or loss of turbidity, is shown in column 4. A positive number means the sample became less turbid or clearer than would have been expected from the weighted average.

Example 6

Measurement of Curl Compression

Curl Compression Test

Five 6 inch virgin brown hair swatches are used for each sample of hair gel to be tested. 30% Curl Compression is the amount of force required to deflect a hair swatch curl 30% of it's diameter. 30% Curl Compression is measured using the following procedure.

Procedure
1. Using the 150 mm virgin brown hair swatches, wet each swatch first with water, and comb through swatch 2-3 times with a fine tooth comb to remove tangles. Squeeze excess water from swatches by squeezing them between a thumb and forefinger.
2. Blot off excessive moisture with a paper towel prior to rolling the curl.
3. Apply 0.50 grams of hair gel to each swatch and work it in from top to bottom 10 times, reversing the hair swatch as you do so.
4. Roll the wetted swatch over a 75 mm long-13 mm diameter Teflon mandrel by rolling the hair on top of itself.
5. Remove the rolled hair swatch from the Teflon mandrel and clip it with a single prong hair clip to keep it tight.
6. Dry rolled hair swatch in 50° C. oven for 1 hour. After drying for this period of time, place the rolled hair swatch in a constant temperature room maintained at 22° C./50% relative humidity to condition overnight.

The swatches are tested the next day using a Diastron MTT 160 miniature tensile tester with a Curl Compression jig available from the manufacturer of the instrument (Diastron Ltd. Andover, Hampshire, England). Each rolled hair swatch is placed in the curl compression jig and tested. The Diastron MTT 160 miniature tensile tester compresses the rolled hair swatch 30% of it's diameter at a rate of 20 mm/min. The force, in gram force, is the 30% curl compression for the sample being tested. The 30% curl compression for the five 6 inch swatches is then recorded and an average is determined based on these five swatches. A PVP K90 hair gel is run each time a series of hair gels is evaluated. A PVP K90 normalized 30% curl compression value is determined by the following formula.

$$PVP\ K90\ \text{Normalized Curl Compression} = \frac{\text{average 30\% curl compression for hair gel sample}}{\text{average 30\% curl compression for } PVP\ K90 \text{ hair gel sample}}$$

TABLE 3

Curl Compression Measurements

| Sample # | Curl Compression (Normalized to K90) | Expected Curl Compression | Synergy |
|---|---|---|---|
| 1 | 0.94 | | |
| 2 | 0.83 | | |
| 3 | 0.93 | | |
| 4 | 0.76 | | |
| 5 | 0.85 | 0.90 | −0.05 |
| 6 | 0.88 | 0.87 | 0.01 |
| 7 | 1.00 | 0.94 | 0.06 |
| 8 | 0.91 | 0.93 | −0.02 |
| 9 | 0.9 | 0.88 | 0.02 |
| 10 | 0.75 | 0.82 | −0.07 |
| 11 | 0.86 | 0.89 | −0.03 |
| 12 | 0.72 | 0.89 | −0.17 |
| 13 | 0.81 | 0.92 | −0.11 |
| 14 | 0.98 | 0.86 | 0.12 |
| 15 | 0.77 | 0.82 | −0.05 |
| 16 | 0.98 | 0.85 | 0.13 |

The results in table 3 above show the curl compression of each of the samples. The expected values are a weighted average from each of the ingredients in rows 1 to 4 and the results are in column 3. The synergy (deviation from expected) is shown in column 4 with a positive value meaning that more force was required to compress the curl than would have been expected from the values for the individual ingredients.

Example 7

Determination of % Flake

% Flake Test

Two 250 mm Asian hair swatches are used for each hair gel sample being tested. Hair gel was applied to hair and allowed to dry, combed, then % flake was determined using image analysis.

Procedure
1. Wet each swatch first with water, and comb through swatch 2-3 times with a fine tooth comb to remove tangles. Squeeze excess water from swatches by squeezing them between a thumb and forefinger.
2. Blot off excessive moisture with a paper towel prior to rolling the curl.
3. Apply 0.50 grams of hair gel to each swatch and work it in from top to bottom 10 times, reversing the hair swatch as you do so.
4. Dry hair swatches in an oven at 60° C. for 1 hour. After drying for this period of time, place the hair swatch in a constant temperature room maintained at 22° C./50% relative humidity to condition overnight.
5. Place hair swatch in the comb attachment of an MTS (Eden Prairie, Minn.) Synergie 200 Tensile Tester, then comb the swatch twice at a rate of 300 mm/min.
6. Digital images of the hair were captured using an Optronics (Goleta, Calif.) Microfire digital camera interfaced with an Olympus (Center Valley, Pa.) SZX10 Stereomicroscope at a magnification of 1 with a 10× objective. Five digital images were taken per hair swatch.
7. The digital images were analyzed for flake using Microsuite Analytical Suite 2.6 (Olympus Soft Imaging Solutions GmbH, Munster, Germany). Images were first converted to gray scale, then the grayscale range was adjusted so that all the flake particles were captured. The software then calculated the amount flake (by the grayscale range selected) relative to the area of the entire image. The amount of flake for each hair gel sample is the average 10 images (5 images on 2 hair swatches)

A PVP K90 hair gel is run each time a series of hair gels is evaluated. A normalized PVP/K90 flake value is determined by the following formula.

$$PVP\ K90\ \text{Normalized Flake} = \frac{\text{average \% flake for hair gel sample}}{\text{average \% flake for } PVP\ K90 \text{ hair gel sample}}$$

TABLE 4

Normalized Percent Flake

| Sample | Flake Normalized to K90 | Expected Flake | Synergy |
|---|---|---|---|
| 1 | 0.72 | | |
| 2 | 2.33 | | |
| 3 | 1.91 | | |
| 4 | 1.03 | | |

TABLE 4-continued

| Sample | Flake Normalized to K90 | Expected Flake | Synergy | High Humidity Curl % | Expected Value | Synergy |
|---|---|---|---|---|---|---|
| 1 | | | | 23 | | |
| 2 | | | | 85 | | |
| 3 | | | | 72 | | |
| 4 | | | | 45 | | |
| 5 | 0.84 | 1.26 | 0.42 | 77 | 44 | 33 |
| 6 | 0.98 | 1.79 | 0.81 | 96 | 64 | 32 |
| 7 | 0.67 | 1.12 | 0.45 | 97 | 39 | 58 |
| 8 | 1.01 | 1.51 | 0.50 | n/a | n/a | n/a |
| 9 | 0.55 | 0.82 | 0.27 | 50 | 30 | 20 |
| 10 | 0.72 | 0.93 | 0.21 | 96 | 38 | 58 |
| 11 | 1.05 | 1.59 | 0.54 | 96 | 57 | 39 |
| 12 | 1.19 | 1.89 | 0.70 | n/a | n/a | n/a |
| 13 | 1.01 | 1.48 | 0.47 | 97 | 54 | 43 |
| 14 | 0.99 | 1.44 | 0.45 | 89 | 53 | 37 |
| 15 | 0.76 | 1.52 | 0.76 | 91 | 58 | 33 |
| 16 | 0.48 | 1.12 | 0.64 | 97 | 43 | 55 |

The results in table 4 above shown the actual measured values obtained for each sample. The expected value in column 3 represents a weighted average from each of the ingredients. The synergy value represents the decrease in flake when PVOH and PVF are blended together. The lower the flake value the more desirable the formulation.

Example 8

Measurement of High Humidity Curl Retention

High Humidity Curl Retention

Nine 10.0 inch virgin brown hair swatches are used for each hair gel sample to be tested and an average is determined based on these nine swatches. The curl retention properties of hair fixative polymers of the present invention are compared to each other and commercial benchmarks. The test is conducted at 70° F. (21° C.) and 90 percent Relative Humidity over a period of 24 hours. The procedure allows for statistical analysis of formulation variables.

Procedure
1. Wet hair swatch and comb through 2-3 times to remove snarls.
2. Squeeze out excess water by running the swatch between thumb and index finger.
3. Apply 0.50 grams of hair gel to swatch, gently work into swatch and comb through.
4. Roll swatch on 3" long-½" diameter Teflon mandrel. Carefully remove rolled swatch from mandrel and secure with two hair clips.
5. Dry rolled swatch in oven 120° F. overnight.
6. Remove rolled swatch from oven and let cool to room temperature.
7. Suspend rolled swatch from the bound end of the swatch on a graduated clear transparent curl retention board.
8. Remove clips from rolled swatch and gently unwind with glass rod.
9. Take initial curl height reading $L_o$, then set curl retention boards into the environmental chamber (70° F., 90% relative humidity).
10. Record curl length $L_t$ at 24 hours.

The high humidity curl retention is calculated by the following formula:

$$\% \text{ High Humidity Curl Retention} = (L-L_t)/(L-L_0)*100,$$

Where L=length of hair fully extended, $L_0$=initial curl length, $L_t$=curl length at a given time t.

What is claimed is:

1. A clear hair gel composition comprising a gelling agent and a polymeric fixative, wherein said polymeric fixative comprises a blend of at least one polyvinyl formamide, and a blend of polyvinyl alcohol homopolymers having different amounts of hydrolyzation, wherein the ratio of the polyvinyl alcohol homopolymers to the polyvinyl formamide is from 4:1 to 1:4, and wherein the blend of polyvinyl alcohol homopolymers comprises a 87-89% hydrolyzed polyvinyl alcohol homopolymer and a 98-99% hydrolyzed polyvinyl alcohol homopolymer.

2. The clear hair gel composition of claim 1 wherein said polymer fixative comprises a polyvinyl formamide and one or more polyvinyl alcohol homopolymers present in an amount of from 80 to 20% and the polyvinyl formamide is present in an amount of from 20 to 80% polyvinyl alcohol homopolymer.

3. The clear hair gel composition of claim 1 comprising a polyvinyl alcohol homopolymer having a molecular weight corresponding to a viscosity of 3-35 mPas.

4. The clear hair gel composition of claim 1 wherein the polymer fixative is present in an amount of 0.5 to 15 percent by weight based on the total gel weight.

5. The clear hair gel composition of claim 1 wherein the gelling agent is present in an amount of 0.005 to 1.0 percent by weight based on the total weight of the gel.

6. The clear hair gel composition of claim 1 wherein said gelling agent comprises a cross-linked acrylate polymer.

7. The clear hair gel composition of claim 1 wherein the gel composition has a high humidity curl retention of greater than 50%.

8. The clear hair gel composition of claim 1 wherein the gel composition has a turbidity of less than 20 NTU.

9. The clear hair gel composition of claim 1 wherein the gel composition has a curl compression of greater than 80% of a standard PVP K90 formulation.

10. The clear hair gel composition of claim 1 wherein the gel composition has a flake test value of less than 1.0.

11. A clear hair gel composition comprising: a polymer fixative system and an acrylate cross-linked gelling agent, said polymer fixative system comprising a blend of at least one polyvinyl formamide and a blend of polyvinyl alcohol homopolymers having different amounts of hydrolyzation, wherein the ratio of the polyvinyl alcohol homopolymers to the polyvinyl formamide is from 4:1 to 1:4, and wherein the blend of polyvinyl alcohol homopolymers comprises a 87-89% hydrolyzed polyvinyl alcohol homopolymer and a 98-99% hydrolyzed polyvinyl alcohol homopolymer.

12. A polymeric hair fixative system comprising a blend of at least one polyvinyl formamide and a blend of polyvinyl alcohol homopolymers having different amounts of hydrolyzation, wherein the ratio of the polyvinyl alcohol homopolymers to the polyvinyl formamide is from 4:1 to 1:4, and wherein the blend of polyvinyl alcohol homopolymers comprises a 87-89% hydrolyzed polyvinyl alcohol homopolymer and a 98-99% hydrolyzed polyvinyl alcohol homopolymer.

13. The clear hair gel composition of claim 1 wherein the composition has a molecular weight of 100,000 to 300,000 Daltons.

14. The clear hair gel composition of claim 2 wherein said polymer fixative comprises 60 to 30% polyvinyl formamide and 40 to 70% polyvinyl alcohol homopolymers.

15. The clear hair gel composition of claim 3 wherein the polyvinyl alcohol homopolymer has a molecular weight corresponding to a viscosity of 3-5 mPas.

16. The clear hair gel composition of claim 4 wherein the polymer fixative is present in an amount of 1 to 10 percent by weight based on the total gel weight.

17. The clear hair gel composition of claim 16 wherein the gelling agent is present in an amount of 0.1 to 0.6 percent by weight based on the total weight of the gel.

18. The clear hair gel composition of claim 6 wherein said cross-linked acrylate polymer is neutralized with a neutralizing agent selected from the group consisting of a hydroxide, an amine, and mixtures thereof.

19. The clear hair gel composition of claim 18 wherein the neutralizing agent is selected from the group consisting of triethanol amine, 2-amino-2-methyl-1-propanol, and mixtures thereof.

* * * * *